(12) United States Patent
Valaie

(10) Patent No.: US 8,252,018 B2
(45) Date of Patent: Aug. 28, 2012

(54) HELICAL EMBOLIC PROTECTION DEVICE

(75) Inventor: Arman H. Valaie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 350 days.

(21) Appl. No.: 11/855,593

(22) Filed: Sep. 14, 2007

(65) Prior Publication Data

US 2009/0076538 A1 Mar. 19, 2009

(51) Int. Cl.
*A61M 29/00* (2006.01)

(52) U.S. Cl. ...................................... 606/200

(58) Field of Classification Search .............. 623/1.11; 606/200
See application file for complete search history.

(56) References Cited

U.S. PATENT DOCUMENTS

| | | |
|---|---|---|
| 3,108,593 A | 10/1963 | Glassman |
| 3,334,629 A | 8/1967 | Cohn |
| 3,472,230 A | 10/1969 | Fogarty |
| 3,547,103 A | 12/1970 | Cook |
| 3,635,223 A | 1/1972 | Klieman |
| 3,923,065 A | 12/1975 | Nozick et al. |
| 3,952,747 A | 4/1976 | Kimmell, Jr. |
| 3,978,863 A | 9/1976 | Fettel et al. |
| 3,996,938 A | 12/1976 | Clark, III |
| 4,425,908 A | 1/1984 | Simon |
| 4,456,000 A | 6/1984 | Schjeldahl et al. |
| 4,494,531 A | 1/1985 | Gianturco |
| 4,548,206 A | 10/1985 | Osborne |
| 4,561,439 A | 12/1985 | Bishop et al. |
| 4,562,039 A | 12/1985 | Koehler |
| 4,604,094 A | 8/1986 | Shook |
| 4,619,246 A | 10/1986 | Molgaard-Nielsen et al. |
| 4,643,184 A | 2/1987 | Mobin-Uddin |
| 4,646,736 A | 3/1987 | Auth |
| 4,650,472 A | 3/1987 | Bates |
| 4,665,906 A | 5/1987 | Jervis |
| 4,669,464 A | 6/1987 | Sulepov |
| 4,688,553 A | 8/1987 | Metals |

(Continued)

FOREIGN PATENT DOCUMENTS

DE    3429850 A1    2/1986

(Continued)

OTHER PUBLICATIONS

Rubicon Embolic Filter, The Next Generation of EM, Rubicon Medical, www.rubiconmed.com, Jun. 28, 2005.

(Continued)

*Primary Examiner* — Gary Jackson
*Assistant Examiner* — Chirstopher Schubert
(74) *Attorney, Agent, or Firm* — Brinks Hofer Gilson & Lione (57) ABSTRACT

An embolic protection device for capturing emboli during treatment of a stenotic lesion in a body vessel is disclosed. The device comprises an elongated shaft having a proximal portion and a distal portion extending from the proximal portion. The device further comprises an expandable filter formed helically about the distal portion of the elongated shaft. The expandable filter is configured to helically close defining a collapsed state for delivery and retrievable of the device. The expandable filter is configured to helically open defining an expanded state for capturing emboli during treatment of the stenotic lesion in the body vessel. The expandable filter has at least one filter portion helically extending from the elongated shaft at a predetermined angle defining an opening when the filter is in the expanded state.

21 Claims, 5 Drawing Sheets

U.S. PATENT DOCUMENTS

| | | | |
|---|---|---|---|
| 4,723,549 A | 2/1988 | Wholey et al. | |
| 4,727,873 A | 3/1988 | Mobin-Uddin | |
| 4,732,152 A | 3/1988 | Wallsten et al. | |
| 4,817,600 A | 4/1989 | Herms et al. | |
| 4,824,435 A | 4/1989 | Giesy et al. | |
| 4,832,055 A | 5/1989 | Palestrant | |
| 4,848,343 A | 7/1989 | Wallsten et al. | |
| 4,873,978 A | 10/1989 | Ginsburg | |
| 4,943,297 A | 7/1990 | Saveliev et al. | |
| 4,957,501 A | 9/1990 | Lahille et al. | |
| 4,990,156 A | 2/1991 | Lefebvre | |
| 4,998,916 A | 3/1991 | Hammerslag et al. | |
| 5,053,008 A | 10/1991 | Bajaj | |
| 5,059,205 A | 10/1991 | El-Nounou et al. | |
| 5,069,226 A | 12/1991 | Yamauchi et al. | |
| 5,078,726 A | 1/1992 | Kreamer | |
| 5,100,423 A | 3/1992 | Fearnot | |
| 5,108,418 A | 4/1992 | Lefebvre | |
| 5,108,419 A * | 4/1992 | Reger et al. | 606/200 |
| 5,112,347 A | 5/1992 | Taheri | |
| 5,129,890 A | 7/1992 | Bates et al. | |
| 5,129,910 A | 7/1992 | Phan et al. | |
| 5,133,733 A | 7/1992 | Rasmussen et al. | |
| 5,147,379 A | 9/1992 | Sabbaghian et al. | |
| 5,152,777 A | 10/1992 | Goldberg | |
| 5,160,342 A | 11/1992 | Reger | |
| 5,163,927 A | 11/1992 | Woker et al. | |
| 5,203,772 A | 4/1993 | Hammerslag et al. | |
| 5,234,458 A | 8/1993 | Metais | |
| 5,242,462 A | 9/1993 | El-Nounou | |
| 5,243,996 A | 9/1993 | Hall | |
| 5,251,640 A | 10/1993 | Osborne | |
| 5,263,964 A | 11/1993 | Purdy | |
| 5,300,086 A | 4/1994 | Gory et al. | |
| 5,324,304 A | 6/1994 | Rasmussen | |
| 5,329,942 A | 7/1994 | Gunther et al. | |
| 5,344,427 A | 9/1994 | Cottenceau et al. | |
| 5,350,397 A | 9/1994 | Palermo et al. | |
| 5,350,398 A | 9/1994 | Pavcnik et al. | |
| 5,364,345 A | 11/1994 | Lowery et al. | |
| 5,370,657 A | 12/1994 | Irie | |
| 5,375,612 A | 12/1994 | Cottenceau et al. | |
| 5,383,887 A | 1/1995 | Nadal | |
| 5,413,586 A | 5/1995 | Dibie et al. | |
| 5,415,630 A | 5/1995 | Gory et al. | |
| 5,417,708 A | 5/1995 | Hall et al. | |
| 5,451,233 A | 9/1995 | Yock | |
| 5,458,573 A | 10/1995 | Summers | |
| 5,522,881 A | 6/1996 | Lentz | |
| 5,527,338 A | 6/1996 | Purdy | |
| 5,531,788 A | 7/1996 | Dibie et al. | |
| 5,549,551 A | 8/1996 | Peacock et al. | |
| 5,549,626 A | 8/1996 | Miller et al. | |
| 5,556,414 A | 9/1996 | Turi | |
| 5,562,698 A | 10/1996 | Parker | |
| 5,591,195 A | 1/1997 | Taheri et al. | |
| 5,601,595 A | 2/1997 | Smith | |
| 5,624,461 A | 4/1997 | Mariant | |
| 5,626,605 A | 5/1997 | Irie et al. | |
| 5,630,797 A | 5/1997 | Diedrich et al. | |
| 5,634,942 A | 6/1997 | Chevillon et al. | |
| 5,649,953 A | 7/1997 | Lefebvre | |
| 5,662,703 A | 9/1997 | Yurek et al. | |
| 5,669,933 A | 9/1997 | Simon et al. | |
| 5,681,347 A | 10/1997 | Cathcart et al. | |
| 5,690,642 A | 11/1997 | Osborne et al. | |
| 5,690,667 A | 11/1997 | Gia | |
| 5,693,067 A | 12/1997 | Purdy | |
| 5,693,087 A | 12/1997 | Parodi | |
| 5,695,518 A | 12/1997 | Laerum | |
| 5,695,519 A | 12/1997 | Summers et al. | |
| 5,700,253 A | 12/1997 | Parker | |
| 5,709,704 A | 1/1998 | Nott et al. | |
| 5,713,853 A | 2/1998 | Clark et al. | |
| 5,720,764 A | 2/1998 | Naderlinger | |
| 5,725,550 A | 3/1998 | Nadal | |
| 5,738,667 A | 4/1998 | Solar | |
| 5,746,767 A | 5/1998 | Smith | |
| 5,755,772 A | 5/1998 | Evans et al. | |
| 5,755,790 A | 5/1998 | Chevillon et al. | |
| 5,766,203 A | 6/1998 | Imran et al. | |
| 5,769,816 A | 6/1998 | Barbut et al. | |
| 5,769,871 A | 6/1998 | Mers et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,027 A | 9/1998 | Hassett et al. | |
| 5,814,064 A | 9/1998 | Daniel et al. | |
| 5,820,592 A | 10/1998 | Hammerslag | |
| 5,827,324 A | 10/1998 | Cassell et al. | |
| 5,830,230 A | 11/1998 | Berryman et al. | |
| 5,836,968 A | 11/1998 | Simon et al. | |
| 5,836,969 A | 11/1998 | Kim et al. | |
| 5,846,260 A | 12/1998 | Maahs | |
| 5,853,420 A | 12/1998 | Chevillon et al. | |
| 5,876,367 A | 3/1999 | Kaganov et al. | |
| 5,882,329 A | 3/1999 | Patterson et al. | |
| 5,893,869 A | 4/1999 | Barnhart et al. | |
| 5,895,391 A | 4/1999 | Farnholtz | |
| 5,895,399 A | 4/1999 | Barbut et al. | |
| 5,895,410 A | 4/1999 | Forber et al. | |
| 5,908,435 A | 6/1999 | Samuels | |
| 5,910,154 A | 6/1999 | Tsugita et al. | |
| 5,911,702 A | 6/1999 | Romley et al. | |
| 5,911,704 A | 6/1999 | Humes | |
| 5,911,717 A | 6/1999 | Jacobsen et al. | |
| 5,911,734 A | 6/1999 | Tsugita et al. | |
| 5,919,224 A | 7/1999 | Thompson et al. | |
| 5,925,062 A | 7/1999 | Purdy | |
| 5,925,063 A | 7/1999 | Khosravi | |
| 5,928,260 A | 7/1999 | Chin et al. | |
| 5,928,261 A | 7/1999 | Ruiz | |
| 5,938,683 A | 8/1999 | Lefebvre | |
| 5,941,896 A | 8/1999 | Kerr | |
| 5,944,728 A | 8/1999 | Bates | |
| 5,947,985 A | 9/1999 | Imran | |
| 5,947,995 A | 9/1999 | Samuels | |
| 5,948,017 A | 9/1999 | Taheri | |
| 5,951,567 A | 9/1999 | Javier, Jr. et al. | |
| 5,954,741 A | 9/1999 | Fox | |
| 5,954,742 A | 9/1999 | Osypka | |
| 5,954,745 A | 9/1999 | Gertler et al. | |
| 5,968,057 A | 10/1999 | Taheri | |
| 5,968,071 A | 10/1999 | Chevillon et al. | |
| 5,972,019 A | 10/1999 | Engelson et al. | |
| 5,976,162 A | 11/1999 | Doan et al. | |
| 5,976,172 A | 11/1999 | Homsma et al. | |
| 5,980,555 A | 11/1999 | Barbut et al. | |
| 5,984,947 A | 11/1999 | Smith | |
| 5,989,281 A | 11/1999 | Barbut et al. | |
| 6,001,118 A | 12/1999 | Daniel et al. | |
| 6,007,557 A | 12/1999 | Ambrisco et al. | |
| 6,007,558 A | 12/1999 | Ravenscroft et al. | |
| 6,010,522 A | 1/2000 | Barbut et al. | |
| 6,013,093 A | 1/2000 | Nott et al. | |
| 6,015,424 A | 1/2000 | Rosenbluth et al. | |
| 6,027,520 A | 2/2000 | Tsugita et al. | |
| 6,036,717 A | 3/2000 | Mers Kelly et al. | |
| 6,036,720 A | 3/2000 | Abrams et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,745 A | 5/2000 | Gelbfish | |
| 6,059,813 A | 5/2000 | Vrba et al. | |
| 6,059,814 A | 5/2000 | Ladd | |
| 6,063,113 A | 5/2000 | Kavteladze et al. | |
| 6,066,158 A | 5/2000 | Engelson et al. | |
| 6,068,645 A | 5/2000 | Tu | |
| 6,074,357 A | 6/2000 | Kaganov et al. | |
| 6,077,274 A | 6/2000 | Ouchi et al. | |
| 6,080,178 A | 6/2000 | Meglin | |
| 6,083,239 A | 7/2000 | Addis | |
| 6,086,577 A | 7/2000 | Ken et al. | |
| 6,086,605 A | 7/2000 | Barbut et al. | |
| 6,093,199 A | 7/2000 | Brown et al. | |

| Patent No. | Kind | Date | Inventor |
|---|---|---|---|
| 6,096,053 | A | 8/2000 | Bates |
| 6,096,070 | A | 8/2000 | Ragheb et al. |
| 6,099,549 | A | 8/2000 | Bosma et al. |
| 6,106,497 | A | 8/2000 | Wang |
| 6,126,672 | A | 10/2000 | Berryman et al. |
| 6,126,673 | A | 10/2000 | Kim et al. |
| 6,129,739 | A | 10/2000 | Khosravi |
| 6,136,016 | A | 10/2000 | Barbut et al. |
| 6,146,396 | A | 11/2000 | Konya et al. |
| 6,146,404 | A | 11/2000 | Kim et al. |
| 6,152,931 | A | 11/2000 | Nadal et al. |
| 6,152,946 | A | 11/2000 | Broome et al. |
| 6,152,947 | A | 11/2000 | Ambrisco et al. |
| 6,156,061 | A | 12/2000 | Wallace et al. |
| 6,159,230 | A | 12/2000 | Samuels |
| 6,165,179 | A | 12/2000 | Cathcart et al. |
| 6,165,198 | A | 12/2000 | McGurk et al. |
| 6,165,199 | A | 12/2000 | Barbut |
| 6,165,200 | A | 12/2000 | Tsugita et al. |
| 6,168,579 | B1 | 1/2001 | Tsugita et al. |
| 6,168,603 | B1 | 1/2001 | Leslie et al. |
| 6,168,610 | B1 | 1/2001 | Marin et al. |
| 6,168,622 | B1 | 1/2001 | Mazzocchi |
| 6,171,327 | B1 | 1/2001 | Daniel et al. |
| 6,171,328 | B1 | 1/2001 | Addis |
| 6,174,318 | B1 | 1/2001 | Bates et al. |
| 6,179,851 | B1 | 1/2001 | Barbut et al. |
| 6,179,859 | B1 | 1/2001 | Bates et al. |
| 6,179,860 | B1 | 1/2001 | Fulton, III et al. |
| 6,179,861 | B1 | 1/2001 | Khosravi et al. |
| 6,187,025 | B1 | 2/2001 | Machek |
| 6,193,739 | B1 | 2/2001 | Chevillon et al. |
| 6,203,561 | B1 | 3/2001 | Ramee et al. |
| 6,206,931 | B1 | 3/2001 | Cook et al. |
| 6,214,025 | B1 | 4/2001 | Thistle et al. |
| 6,214,026 | B1 | 4/2001 | Lepak et al. |
| 6,221,091 | B1 | 4/2001 | Khosravi |
| 6,224,620 | B1 | 5/2001 | Maahs |
| 6,231,588 | B1 | 5/2001 | Zadno-Azizi |
| 6,231,589 | B1 | 5/2001 | Wessman et al. |
| 6,235,044 | B1 | 5/2001 | Root et al. |
| 6,235,045 | B1 | 5/2001 | Barbut et al. |
| 6,238,412 | B1 | 5/2001 | Dubrul et al. |
| 6,241,746 | B1 | 6/2001 | Bosma et al. |
| 6,245,087 | B1 | 6/2001 | Addis |
| 6,245,088 | B1 | 6/2001 | Lowery |
| 6,245,089 | B1 | 6/2001 | Daniel et al. |
| 6,251,092 | B1 | 6/2001 | Qin et al. |
| 6,251,122 | B1 | 6/2001 | Tsukernik |
| 6,254,550 | B1 | 7/2001 | McNamara et al. |
| 6,254,633 | B1 | 7/2001 | Pinchuk et al. |
| 6,258,026 | B1 | 7/2001 | Ravenscroft et al. |
| 6,258,115 | B1 | 7/2001 | Dubrul |
| 6,258,120 | B1 | 7/2001 | McKenzie et al. |
| 6,261,305 | B1 | 7/2001 | Marotta et al. |
| 6,264,672 | B1 | 7/2001 | Fisher |
| 6,267,776 | B1 | 7/2001 | O'Connell |
| 6,267,777 | B1 | 7/2001 | Bosma et al. |
| 6,273,900 | B1 | 8/2001 | Nott et al. |
| 6,273,901 | B1 | 8/2001 | Whitcher et al. |
| 6,277,125 | B1 | 8/2001 | Barry et al. |
| 6,277,126 | B1 | 8/2001 | Barry et al. |
| 6,277,138 | B1 | 8/2001 | Levinson et al. |
| 6,277,139 | B1 | 8/2001 | Levinson et al. |
| 6,280,451 | B1 | 8/2001 | Bates et al. |
| 6,287,321 | B1 | 9/2001 | Jang |
| 6,290,710 | B1 | 9/2001 | Cryer et al. |
| 6,299,604 | B1 | 10/2001 | Ragheb et al. |
| 6,306,163 | B1 | 10/2001 | Fitz |
| 6,309,399 | B1 | 10/2001 | Barbut et al. |
| 6,312,444 | B1 | 11/2001 | Barbut |
| 6,319,268 | B1 | 11/2001 | Ambrisco et al. |
| 6,325,815 | B1 | 12/2001 | Kusleika et al. |
| 6,325,816 | B1 | 12/2001 | Fulton, III et al. |
| 6,328,755 | B1 | 12/2001 | Marshall |
| 6,331,183 | B1 | 12/2001 | Suon |
| 6,331,184 | B1 | 12/2001 | Abrams |
| 6,334,864 | B1 | 1/2002 | Amplatz et al. |
| 6,336,934 | B1 | 1/2002 | Gilson et al. |
| 6,338,739 | B1 | 1/2002 | Datta et al. |
| 6,340,364 | B2 | 1/2002 | Kanesaka |
| 6,342,062 | B1 | 1/2002 | Suon et al. |
| 6,342,063 | B1 | 1/2002 | DeVries et al. |
| 6,344,048 | B1 | 2/2002 | Chin et al. |
| 6,344,049 | B1 | 2/2002 | Levinson et al. |
| 6,346,116 | B1 | 2/2002 | Brooks et al. |
| 6,348,041 | B1 | 2/2002 | Klint |
| 6,348,063 | B1 | 2/2002 | Yassour et al. |
| 6,355,051 | B1 | 3/2002 | Sisskind et al. |
| 6,358,228 | B1 | 3/2002 | Tubman et al. |
| 6,361,545 | B1 | 3/2002 | Macoviak et al. |
| 6,361,546 | B1 | 3/2002 | Khosravi |
| 6,361,547 | B1 | 3/2002 | Hieshima |
| 6,364,895 | B1 | 4/2002 | Greenhalgh |
| 6,364,896 | B1 | 4/2002 | Addis |
| 6,368,338 | B1 | 4/2002 | Konya et al. |
| 6,371,961 | B1 | 4/2002 | Osborne et al. |
| 6,371,969 | B1 | 4/2002 | Tsugita et al. |
| 6,371,970 | B1 | 4/2002 | Khosravi et al. |
| 6,371,971 | B1 | 4/2002 | Tsugita et al. |
| 6,375,670 | B1 | 4/2002 | Greenhalgh |
| 6,379,374 | B1 | 4/2002 | Hieshima et al. |
| 6,380,457 | B1 | 4/2002 | Yurek et al. |
| 6,383,146 | B1 | 5/2002 | Klint |
| 6,383,171 | B1 | 5/2002 | Gifford et al. |
| 6,383,174 | B1 | 5/2002 | Eder |
| 6,383,193 | B1 | 5/2002 | Cathcart et al. |
| 6,383,196 | B1 | 5/2002 | Leslie et al. |
| 6,383,205 | B1 | 5/2002 | Samson et al. |
| 6,383,206 | B1 | 5/2002 | Gillick et al. |
| 6,391,044 | B1 | 5/2002 | Yadav et al. |
| 6,391,045 | B1 | 5/2002 | Kim et al. |
| 6,391,052 | B2 | 5/2002 | Buirge et al. |
| 6,395,014 | B1 | 5/2002 | Macoviak et al. |
| 6,402,771 | B1 | 6/2002 | Palmer et al. |
| 6,402,772 | B1 | 6/2002 | Amplatz et al. |
| 6,409,742 | B1 | 6/2002 | Fulton, III et al. |
| 6,413,235 | B1 | 7/2002 | Parodi |
| 6,416,530 | B2 | 7/2002 | DeVries et al. |
| 6,419,686 | B1 | 7/2002 | McLeod et al. |
| 6,423,052 | B1 | 7/2002 | Escano |
| 6,423,086 | B1 | 7/2002 | Barbut et al. |
| 6,425,909 | B1 | 7/2002 | Dieck et al. |
| 6,428,557 | B1 | 8/2002 | Hilaire |
| 6,428,558 | B1 | 8/2002 | Jones et al. |
| 6,428,559 | B1 | 8/2002 | Johnson |
| 6,432,122 | B1 | 8/2002 | Gilson et al. |
| 6,436,112 | B2 | 8/2002 | Wensel et al. |
| 6,436,120 | B1 | 8/2002 | Meglin |
| 6,436,121 | B1 | 8/2002 | Blom |
| 6,443,926 | B1 | 9/2002 | Kletschka |
| 6,443,971 | B1 | 9/2002 | Boylan et al. |
| 6,443,972 | B1 | 9/2002 | Bosma et al. |
| 6,447,530 | B1 | 9/2002 | Ostrovsky et al. |
| 6,447,531 | B1 | 9/2002 | Amplatz |
| 6,454,775 | B1 | 9/2002 | Demarais et al. |
| 6,458,139 | B1 | 10/2002 | Palmer et al. |
| 6,458,145 | B1 | 10/2002 | Ravenscroft et al. |
| 6,461,370 | B1 | 10/2002 | Gray et al. |
| 6,468,290 | B1 | 10/2002 | Weldon et al. |
| 6,468,291 | B2 | 10/2002 | Bates et al. |
| 6,482,222 | B1 | 11/2002 | Bruckheimer et al. |
| 6,485,456 | B1 | 11/2002 | Kletschka |
| 6,485,500 | B1 | 11/2002 | Kokish et al. |
| 6,485,501 | B1 | 11/2002 | Green |
| 6,485,502 | B1 | 11/2002 | Don Michael et al. |
| 6,491,712 | B1 | 12/2002 | O'Connor |
| 6,494,895 | B2 | 12/2002 | Addis |
| 6,497,709 | B1 | 12/2002 | Heath |
| 6,499,487 | B1 | 12/2002 | McKenzie et al. |
| 6,500,166 | B1 | 12/2002 | Zadno Azizi et al. |
| 6,500,191 | B2 | 12/2002 | Addis |
| 6,502,606 | B2 | 1/2003 | Klint |
| 6,506,203 | B1 | 1/2003 | Boyle et al. |
| 6,506,205 | B2 | 1/2003 | Goldberg et al. |
| 6,508,826 | B2 | 1/2003 | Murphy et al. |
| 6,511,492 | B1 | 1/2003 | Rosenbluth et al. |
| 6,511,496 | B1 | 1/2003 | Huter et al. |

| Patent | Kind | Date | Inventor |
|---|---|---|---|
| 6,511,497 | B1 | 1/2003 | Braun et al. |
| 6,511,503 | B1 | 1/2003 | Burkett et al. |
| 6,514,273 | B1 | 2/2003 | Voss et al. |
| 6,517,559 | B1 | 2/2003 | O'Connell |
| 6,520,978 | B1 | 2/2003 | Blackledge et al. |
| 6,527,746 | B1 | 3/2003 | Oslund et al. |
| 6,527,791 | B2 | 3/2003 | Fisher |
| 6,527,962 | B1 | 3/2003 | Nadal |
| 6,530,935 | B2 | 3/2003 | Wensel et al. |
| 6,530,939 | B1 | 3/2003 | Hopkins et al. |
| 6,530,940 | B2 | 3/2003 | Fisher |
| 6,533,770 | B1 | 3/2003 | Lepulu et al. |
| 6,533,800 | B1 | 3/2003 | Barbut |
| 6,537,293 | B1 | 3/2003 | Berryman et al. |
| 6,537,294 | B1 | 3/2003 | Boyle et al. |
| 6,537,296 | B2 | 3/2003 | Levinson et al. |
| 6,537,297 | B2 | 3/2003 | Tsugita et al. |
| 6,540,722 | B1 | 4/2003 | Boyle et al. |
| 6,540,767 | B1 | 4/2003 | Walak et al. |
| 6,540,768 | B1 | 4/2003 | Diaz et al. |
| 6,544,221 | B1 | 4/2003 | Kokish et al. |
| 6,544,276 | B1 | 4/2003 | Azizi |
| 6,544,278 | B1 | 4/2003 | Vrba et al. |
| 6,544,279 | B1 | 4/2003 | Hopkins et al. |
| 6,544,280 | B1 | 4/2003 | Daniel et al. |
| 6,547,759 | B1 | 4/2003 | Fisher |
| 6,551,303 | B1 | 4/2003 | Van Tassel et al. |
| 6,551,341 | B2 | 4/2003 | Boylan et al. |
| 6,551,342 | B1 | 4/2003 | Shen et al. |
| 6,554,849 | B1 | 4/2003 | Jones et al. |
| 6,558,404 | B2 | 5/2003 | Tsukernik |
| 6,558,405 | B1 | 5/2003 | McInnes |
| 6,558,406 | B2 | 5/2003 | Okada |
| 6,562,058 | B2 | 5/2003 | Seguin et al. |
| 6,565,591 | B2 | 5/2003 | Brady et al. |
| 6,569,147 | B1 | 5/2003 | Evans et al. |
| 6,569,183 | B1 | 5/2003 | Kim et al. |
| 6,569,184 | B2 | 5/2003 | Huter |
| 6,575,995 | B1 | 6/2003 | Denison et al. |
| 6,575,996 | B1 | 6/2003 | Denison et al. |
| 6,575,997 | B1 | 6/2003 | Palmer et al. |
| 6,579,303 | B2 | 6/2003 | Amplatz |
| 6,582,396 | B1 | 6/2003 | Parodi |
| 6,582,447 | B1 | 6/2003 | Patel et al. |
| 6,582,448 | B1 | 6/2003 | Boyle et al. |
| 6,589,227 | B2 | 7/2003 | Klint |
| 6,589,230 | B2 | 7/2003 | Gia et al. |
| 6,589,263 | B1 | 7/2003 | Hopkins et al. |
| 6,589,264 | B1 | 7/2003 | Barbut et al. |
| 6,589,265 | B1 | 7/2003 | Palmer et al. |
| 6,589,266 | B2 | 7/2003 | Whitcher et al. |
| 6,592,546 | B1 | 7/2003 | Barbut et al. |
| 6,592,606 | B2 | 7/2003 | Huter et al. |
| 6,592,616 | B1 | 7/2003 | Stack et al. |
| 6,595,983 | B2 | 7/2003 | Voda |
| 6,596,011 | B2 | 7/2003 | Johnson et al. |
| 6,599,275 | B1 | 7/2003 | Fischer, Jr. |
| 6,599,307 | B1 | 7/2003 | Huter et al. |
| 6,599,308 | B2 | 7/2003 | Amplatz |
| 6,602,271 | B2 | 8/2003 | Adams et al. |
| 6,602,273 | B2 | 8/2003 | Marshall |
| 6,602,280 | B2 | 8/2003 | Chobotov |
| 6,605,102 | B1 | 8/2003 | Mazzocchi et al. |
| 6,607,506 | B2 | 8/2003 | Kletschka |
| 6,610,077 | B1 | 8/2003 | Hancock et al. |
| 6,611,720 | B2 | 8/2003 | Hata et al. |
| 6,613,074 | B1 | 9/2003 | Mitelberg et al. |
| 6,616,679 | B1 | 9/2003 | Khosravi et al. |
| 6,616,680 | B1 | 9/2003 | Thielen |
| 6,616,681 | B2 | 9/2003 | Hanson et al. |
| 6,616,682 | B2 | 9/2003 | Joergensen et al. |
| 6,620,148 | B1 | 9/2003 | Tsugita |
| 6,620,182 | B1 | 9/2003 | Khosravi et al. |
| 6,623,450 | B1 | 9/2003 | Dutta |
| 6,623,506 | B2 | 9/2003 | McGuckin, Jr. et al. |
| 6,629,953 | B1 | 10/2003 | Boyd |
| 6,635,068 | B1 | 10/2003 | Dubrul et al. |
| 6,635,069 | B1 | 10/2003 | Teoh et al. |
| 6,635,070 | B2 | 10/2003 | Evans et al. |
| 6,638,293 | B1 | 10/2003 | Makower et al. |
| 6,638,294 | B1 | 10/2003 | Palmer |
| 6,638,372 | B1 | 10/2003 | Abrams et al. |
| 6,641,590 | B1 | 11/2003 | Palmer et al. |
| 6,641,605 | B1 | 11/2003 | Stergiopulos |
| 6,645,160 | B1 | 11/2003 | Heesch |
| 6,645,220 | B1 | 11/2003 | Huter et al. |
| 6,645,221 | B1 | 11/2003 | Richter |
| 6,645,222 | B1 | 11/2003 | Parodi et al. |
| 6,645,223 | B2 | 11/2003 | Boyle et al. |
| 6,645,224 | B2 | 11/2003 | Gilson et al. |
| 6,652,554 | B1 | 11/2003 | Wholey et al. |
| 6,652,557 | B1 | 11/2003 | MacDonald |
| 6,652,558 | B2 | 11/2003 | Patel et al. |
| 6,656,201 | B2 | 12/2003 | Ferrera et al. |
| 6,656,202 | B2 | 12/2003 | Papp et al. |
| 6,656,203 | B2 | 12/2003 | Roth et al. |
| 6,656,204 | B2 | 12/2003 | Ambrisco et al. |
| 6,656,351 | B2 | 12/2003 | Boyle |
| 6,660,021 | B1 | 12/2003 | Palmer et al. |
| 6,663,613 | B1 | 12/2003 | Evans et al. |
| 6,663,650 | B2 | 12/2003 | Sepetka et al. |
| 6,663,651 | B2 | 12/2003 | Krolik et al. |
| 6,663,652 | B2 | 12/2003 | Daniel et al. |
| 6,676,682 | B1 * | 1/2004 | Tsugita et al. ............... 606/200 |
| 6,679,902 | B1 | 1/2004 | Boyle et al. |
| 6,689,144 | B2 | 2/2004 | Gerberding |
| 6,695,813 | B1 | 2/2004 | Boyle et al. |
| 6,695,865 | B2 | 2/2004 | Boyle et al. |
| 6,702,834 | B1 | 3/2004 | Boylan et al. |
| 6,709,450 | B2 | 3/2004 | Kang et al. |
| 6,712,835 | B2 | 3/2004 | Mazzocchi et al. |
| 6,716,207 | B2 | 4/2004 | Farnholtz |
| 6,716,231 | B1 | 4/2004 | Rafiee et al. |
| 6,726,701 | B2 | 4/2004 | Gilson et al. |
| 6,730,064 | B2 | 5/2004 | Ragheb et al. |
| 6,755,855 | B2 | 6/2004 | Yurek et al. |
| 6,755,856 | B2 | 6/2004 | Fierens et al. |
| 6,758,855 | B2 | 7/2004 | Fulton, III et al. |
| 6,761,727 | B1 | 7/2004 | Ladd |
| 6,773,446 | B1 | 8/2004 | Dwyer et al. |
| 6,773,448 | B2 | 8/2004 | Kusleika et al. |
| 6,774,278 | B1 | 8/2004 | Ragheb et al. |
| 6,780,175 | B1 | 8/2004 | Sachdeva et al. |
| 6,793,667 | B2 | 9/2004 | Hebert et al. |
| 6,793,668 | B1 | 9/2004 | Fisher |
| 6,833,002 | B2 | 12/2004 | Stack et al. |
| 6,866,677 | B2 | 3/2005 | Douk et al. |
| 6,896,691 | B2 | 5/2005 | Boylan et al. |
| 6,932,831 | B2 | 8/2005 | Forber |
| 6,942,682 | B2 | 9/2005 | Vrba et al. |
| 6,955,685 | B2 | 10/2005 | Escamilla et al. |
| 6,964,670 | B1 | 11/2005 | Shah et al. |
| 6,964,674 | B1 | 11/2005 | Matsuura et al. |
| 6,969,396 | B2 | 11/2005 | Krolik et al. |
| 6,991,641 | B2 | 1/2006 | Diaz et al. |
| 7,097,651 | B2 | 8/2006 | Harrison et al. |
| 7,128,073 | B1 | 10/2006 | Van der Burg et al. |
| 7,189,249 | B2 | 3/2007 | Hart et al. |
| 7,204,847 | B1 * | 4/2007 | Gambale ............... 623/1.14 |
| 7,255,687 | B2 | 8/2007 | Huang et al. |
| 7,285,130 | B2 | 10/2007 | Austin |
| 7,306,619 | B1 | 12/2007 | Palmer |
| 7,371,248 | B2 | 5/2008 | Dapolito et al. |
| 7,393,358 | B2 | 7/2008 | Malewicz |
| 7,766,934 | B2 | 8/2010 | Pal et al. |
| 2001/0000799 | A1 | 5/2001 | Wessman et al. |
| 2001/0001817 | A1 | 5/2001 | Humes |
| 2001/0005789 | A1 | 6/2001 | Root et al. |
| 2001/0007947 | A1 | 7/2001 | Kanesaka |
| 2001/0011181 | A1 | 8/2001 | DiMatteo |
| 2001/0011182 | A1 | 8/2001 | Dubrul et al. |
| 2001/0012951 | A1 | 8/2001 | Bates et al. |
| 2001/0016755 | A1 | 8/2001 | Addis |
| 2001/0020175 | A1 | 9/2001 | Yassour et al. |
| 2001/0023358 | A1 | 9/2001 | Tsukernik |
| 2001/0025187 | A1 | 9/2001 | Okada |
| 2001/0031980 | A1 | 10/2001 | Wensel et al. |
| 2001/0031981 | A1 | 10/2001 | Evans et al. |

| | | | | | | |
|---|---|---|---|---|---|---|
| 2001/0031982 A1 | 10/2001 | Peterson et al. | | 2002/0143361 A1 | 10/2002 | Douk et al. |
| 2001/0039431 A1 | 11/2001 | DeVries et al. | | 2002/0143362 A1 | 10/2002 | Macoviak et al. |
| 2001/0039432 A1 | 11/2001 | Whitcher et al. | | 2002/0151927 A1 | 10/2002 | Douk et al. |
| 2001/0041908 A1 | 11/2001 | Levinson et al. | | 2002/0151928 A1 | 10/2002 | Leslie et al. |
| 2001/0041909 A1 | 11/2001 | Tsugita et al. | | 2002/0156520 A1 | 10/2002 | Boylan et al. |
| 2001/0041928 A1 | 11/2001 | Pavcnik et al. | | 2002/0161389 A1 | 10/2002 | Boyle et al. |
| 2001/0044632 A1 | 11/2001 | Daniel et al. | | 2002/0161390 A1 | 10/2002 | Mouw |
| 2001/0044634 A1 | 11/2001 | Don Michael et al. | | 2002/0161391 A1 | 10/2002 | Murphy et al. |
| 2001/0053921 A1 | 12/2001 | Jang | | 2002/0161392 A1 | 10/2002 | Dubrul |
| 2002/0002384 A1 | 1/2002 | Gilson et al. | | 2002/0161393 A1 | 10/2002 | Demond et al. |
| 2002/0004667 A1 | 1/2002 | Adams et al. | | 2002/0161394 A1 | 10/2002 | Macoviak et al. |
| 2002/0016564 A1 | 2/2002 | Courtney et al. | | 2002/0161395 A1 | 10/2002 | Douk et al. |
| 2002/0016609 A1 | 2/2002 | Wensel et al. | | 2002/0161396 A1 | 10/2002 | Jang et al. |
| 2002/0022858 A1 | 2/2002 | Demond et al. | | 2002/0165557 A1 | 11/2002 | McAlister |
| 2002/0022859 A1 | 2/2002 | Hogendijk | | 2002/0165573 A1 | 11/2002 | Barbut |
| 2002/0026211 A1 | 2/2002 | Khosravi et al. | | 2002/0165576 A1 | 11/2002 | Boyle et al. |
| 2002/0026212 A1 | 2/2002 | Wholey et al. | | 2002/0165598 A1 | 11/2002 | Wahr et al. |
| 2002/0026213 A1 | 2/2002 | Gilson et al. | | 2002/0169472 A1 | 11/2002 | Douk et al. |
| 2002/0032460 A1 | 3/2002 | Kusleika et al. | | 2002/0169474 A1 | 11/2002 | Kusleika et al. |
| 2002/0032461 A1 | 3/2002 | Marshall | | 2002/0173815 A1 | 11/2002 | Hogendijk et al. |
| 2002/0042626 A1 | 4/2002 | Hanson et al. | | 2002/0173819 A1 | 11/2002 | Leeflang et al. |
| 2002/0042627 A1 | 4/2002 | Brady et al. | | 2002/0177872 A1 | 11/2002 | Papp et al. |
| 2002/0045915 A1 | 4/2002 | Balceta et al. | | 2002/0177899 A1 | 11/2002 | Eum et al. |
| 2002/0045916 A1 | 4/2002 | Gray et al. | | 2002/0183781 A1 | 12/2002 | Casey et al. |
| 2002/0045918 A1 | 4/2002 | Suon et al. | | 2002/0183782 A1* | 12/2002 | Tsugita et al. ............... 606/200 |
| 2002/0049452 A1 | 4/2002 | Kurz et al. | | 2002/0183783 A1 | 12/2002 | Shadduck |
| 2002/0049468 A1 | 4/2002 | Streeter et al. | | 2002/0188313 A1 | 12/2002 | Johnson et al. |
| 2002/0052627 A1 | 5/2002 | Boylan et al. | | 2002/0188314 A1 | 12/2002 | Anderson et al. |
| 2002/0058904 A1 | 5/2002 | Boock et al. | | 2002/0193824 A1 | 12/2002 | Boylan et al. |
| 2002/0058911 A1 | 5/2002 | Gilson et al. | | 2002/0193825 A1 | 12/2002 | McGuckin et al. |
| 2002/0058963 A1 | 5/2002 | Vale et al. | | 2002/0193826 A1 | 12/2002 | McGuckin et al. |
| 2002/0058964 A1 | 5/2002 | Addis | | 2002/0193827 A1 | 12/2002 | McGuckin et al. |
| 2002/0062133 A1 | 5/2002 | Gilson et al. | | 2002/0193828 A1 | 12/2002 | Griffin et al. |
| 2002/0062134 A1 | 5/2002 | Barbut et al. | | 2002/0198561 A1 | 12/2002 | Amplatz |
| 2002/0062135 A1 | 5/2002 | Mazzocchi et al. | | 2003/0004536 A1 | 1/2003 | Boylan et al. |
| 2002/0065507 A1 | 5/2002 | Zadno-Azizi | | 2003/0004537 A1 | 1/2003 | Boyle et al. |
| 2002/0068954 A1 | 6/2002 | Foster | | 2003/0004538 A1 | 1/2003 | Secrest et al. |
| 2002/0068955 A1 | 6/2002 | Khosravi | | 2003/0004539 A1 | 1/2003 | Linder et al. |
| 2002/0072764 A1 | 6/2002 | Sepetka et al. | | 2003/0004540 A1 | 1/2003 | Linder et al. |
| 2002/0072765 A1 | 6/2002 | Mazzocchi et al. | | 2003/0004541 A1 | 1/2003 | Linder et al. |
| 2002/0077596 A1 | 6/2002 | McKenzie et al. | | 2003/0004542 A1 | 1/2003 | Wensel et al. |
| 2002/0082558 A1 | 6/2002 | Samson et al. | | 2003/0009146 A1 | 1/2003 | Muni et al. |
| 2002/0082639 A1 | 6/2002 | Broome et al. | | 2003/0009189 A1 | 1/2003 | Gilson et al. |
| 2002/0087187 A1 | 7/2002 | Mazzocchi et al. | | 2003/0009190 A1 | 1/2003 | Kletschka et al. |
| 2002/0090389 A1 | 7/2002 | Humes et al. | | 2003/0009191 A1 | 1/2003 | Wensel et al. |
| 2002/0091407 A1 | 7/2002 | Zadno-Azizi et al. | | 2003/0014072 A1 | 1/2003 | Wensel et al. |
| 2002/0091408 A1 | 7/2002 | Sutton et al. | | 2003/0018354 A1 | 1/2003 | Roth et al. |
| 2002/0091409 A1 | 7/2002 | Sutton et al. | | 2003/0018355 A1 | 1/2003 | Goto et al. |
| 2002/0095170 A1 | 7/2002 | Krolik et al. | | 2003/0023263 A1 | 1/2003 | Krolik et al. |
| 2002/0095171 A1 | 7/2002 | Belef | | 2003/0023264 A1 | 1/2003 | Dieck et al. |
| 2002/0095172 A1 | 7/2002 | Mazzocchi et al. | | 2003/0023265 A1 | 1/2003 | Forber |
| 2002/0095173 A1 | 7/2002 | Mazzocchi et al. | | 2003/0032976 A1 | 2/2003 | Boucek |
| 2002/0095174 A1 | 7/2002 | Tsugita et al. | | 2003/0032977 A1 | 2/2003 | Brady |
| 2002/0099405 A1 | 7/2002 | Yurek et al. | | 2003/0040772 A1 | 2/2003 | Hyodoh et al. |
| 2002/0099407 A1 | 7/2002 | Becker et al. | | 2003/0045897 A1 | 3/2003 | Huter et al. |
| 2002/0099435 A1 | 7/2002 | Stinson | | 2003/0045898 A1 | 3/2003 | Harrison et al. |
| 2002/0103501 A1 | 8/2002 | Diaz et al. | | 2003/0050662 A1 | 3/2003 | Don Michael |
| 2002/0107541 A1 | 8/2002 | Vale et al. | | 2003/0055452 A1 | 3/2003 | Joergensen et al. |
| 2002/0111647 A1 | 8/2002 | Khairkhahan et al. | | 2003/0055480 A1 | 3/2003 | Fischell et al. |
| 2002/0111648 A1 | 8/2002 | Kusleika et al. | | 2003/0060843 A1 | 3/2003 | Boucher |
| 2002/0111649 A1 | 8/2002 | Russo et al. | | 2003/0060844 A1 | 3/2003 | Borillo et al. |
| 2002/0116024 A1 | 8/2002 | Goldberg et al. | | 2003/0065354 A1 | 4/2003 | Boyle et al. |
| 2002/0120226 A1 | 8/2002 | Beck | | 2003/0065355 A1 | 4/2003 | Weber |
| 2002/0120286 A1 | 8/2002 | DoBrava et al. | | 2003/0065356 A1 | 4/2003 | Tsugita et al. |
| 2002/0120287 A1 | 8/2002 | Huter | | 2003/0069596 A1 | 4/2003 | Eskuri |
| 2002/0123720 A1 | 9/2002 | Kusleika et al. | | 2003/0073979 A1 | 4/2003 | Naimark et al. |
| 2002/0123755 A1 | 9/2002 | Lowe et al. | | 2003/0074019 A1 | 4/2003 | Gray et al. |
| 2002/0123759 A1 | 9/2002 | Amplatz | | 2003/0078614 A1 | 4/2003 | Salahieh et al. |
| 2002/0123766 A1 | 9/2002 | Seguin et al. | | 2003/0083608 A1 | 5/2003 | Evans et al. |
| 2002/0128679 A1 | 9/2002 | Turovskiy et al. | | 2003/0083692 A1 | 5/2003 | Vrba et al. |
| 2002/0128680 A1 | 9/2002 | Pavlovic | | 2003/0083693 A1 | 5/2003 | Daniel et al. |
| 2002/0128681 A1 | 9/2002 | Broome et al. | | 2003/0088211 A1 | 5/2003 | Anderson et al. |
| 2002/0133191 A1 | 9/2002 | Khosravi et al. | | 2003/0088266 A1 | 5/2003 | Bowlin |
| 2002/0133192 A1 | 9/2002 | Kusleika et al. | | 2003/0093110 A1 | 5/2003 | Vale |
| 2002/0138094 A1 | 9/2002 | Borillo et al. | | 2003/0093112 A1 | 5/2003 | Addis |
| 2002/0138095 A1 | 9/2002 | Mazzocchi et al. | | 2003/0097094 A1 | 5/2003 | Ouriel et al. |
| 2002/0138096 A1 | 9/2002 | Hieshima | | 2003/0097145 A1 | 5/2003 | Goldberg et al. |
| 2002/0138097 A1 | 9/2002 | Ostrovsky et al. | | 2003/0100917 A1 | 5/2003 | Boyle et al. |
| 2002/0143360 A1 | 10/2002 | Douk et al. | | 2003/0100918 A1 | 5/2003 | Duane |

| | | |
|---|---|---|
| 2003/0100919 A1 | 5/2003 | Hopkins et al. |
| 2003/0105472 A1 | 6/2003 | McAlister |
| 2003/0105484 A1 | 6/2003 | Boyle et al. |
| 2003/0105486 A1 | 6/2003 | Murphy et al. |
| 2003/0109824 A1 | 6/2003 | Anderson et al. |
| 2003/0109897 A1 | 6/2003 | Walak et al. |
| 2003/0109916 A1 | 6/2003 | Don Michael |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0120304 A1 | 6/2003 | Kaganov et al. |
| 2003/0125764 A1 | 7/2003 | Brady et al. |
| 2003/0125765 A1 | 7/2003 | Blackledge et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135232 A1 | 7/2003 | Douk et al. |
| 2003/0135233 A1 | 7/2003 | Bates et al. |
| 2003/0139764 A1 | 7/2003 | Levinson et al. |
| 2003/0139765 A1 | 7/2003 | Patel et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0153944 A1 | 8/2003 | Phung et al. |
| 2003/0153945 A1 | 8/2003 | Patel et al. |
| 2003/0158518 A1 | 8/2003 | Schonholz et al. |
| 2003/0158574 A1 | 8/2003 | Esch et al. |
| 2003/0158575 A1 | 8/2003 | Boylan et al. |
| 2003/0163158 A1 | 8/2003 | White |
| 2003/0163159 A1 | 8/2003 | Patel et al. |
| 2003/0167068 A1 | 9/2003 | Amplatz |
| 2003/0167069 A1 | 9/2003 | Gonzales et al. |
| 2003/0171769 A1 | 9/2003 | Barbut |
| 2003/0171770 A1 | 9/2003 | Kusleika et al. |
| 2003/0171771 A1 | 9/2003 | Anderson et al. |
| 2003/0171772 A1 | 9/2003 | Amplatz |
| 2003/0171800 A1 | 9/2003 | Bicek et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176887 A1 | 9/2003 | Petersen |
| 2003/0176888 A1 | 9/2003 | O'Connell |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191492 A1 | 10/2003 | Gellman et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199917 A1 | 10/2003 | Knudson et al. |
| 2003/0199918 A1 | 10/2003 | Patel et al. |
| 2003/0199919 A1 | 10/2003 | Palmer et al. |
| 2003/0199920 A1 | 10/2003 | Boylan et al. |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0204203 A1 | 10/2003 | Khairkhahan et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0208253 A1 | 11/2003 | Beyer et al. |
| 2003/0212428 A1 | 11/2003 | Richter |
| 2003/0212429 A1 | 11/2003 | Keegan et al. |
| 2003/0212431 A1 | 11/2003 | Brady et al. |
| 2003/0212432 A1 | 11/2003 | Khairkhahan et al. |
| 2003/0212433 A1 | 11/2003 | Ambrisco et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0220667 A1 | 11/2003 | Van der Burg et al. |
| 2003/0225418 A1 | 12/2003 | Esksuri et al. |
| 2003/0225435 A1 | 12/2003 | Huter et al. |
| 2003/0229374 A1 | 12/2003 | Brady et al. |
| 2003/0233117 A1 | 12/2003 | Adams et al. |
| 2004/0006364 A1 | 1/2004 | Ladd |
| 2004/0006370 A1 | 1/2004 | Tsugita |
| 2004/0015152 A1 | 1/2004 | Day |
| 2004/0039412 A1 | 2/2004 | Isshiki et al. |
| 2004/0049226 A1 | 3/2004 | Keegan et al. |
| 2004/0054394 A1 | 3/2004 | Lee |
| 2004/0054395 A1 | 3/2004 | Lee et al. |
| 2004/0059372 A1 | 3/2004 | Tsugita |
| 2004/0064067 A1 | 4/2004 | Ward |
| 2004/0064179 A1 | 4/2004 | Linder et al. |
| 2004/0068271 A1 | 4/2004 | McAlister |
| 2004/0078044 A1 | 4/2004 | Kear et al. |
| 2004/0082962 A1 | 4/2004 | Demarais et al. |
| 2004/0088038 A1 | 5/2004 | Dehnad et al. |
| 2004/0093009 A1 | 5/2004 | Denison et al. |
| 2004/0093012 A1 | 5/2004 | Cully et al. |
| 2004/0093016 A1 | 5/2004 | Root et al. |
| 2004/0093059 A1 | 5/2004 | Lee et al. |
| 2004/0098022 A1 | 5/2004 | Barone |
| 2004/0098026 A1 | 5/2004 | Joergensen et al. |
| 2004/0098033 A1 | 5/2004 | Leeflang et al. |
| 2004/0098112 A1 | 5/2004 | DiMatteo et al. |
| 2004/0102719 A1 | 5/2004 | Keith et al. |
| 2004/0106944 A1 | 6/2004 | Daniel et al. |
| 2004/0116831 A1 | 6/2004 | Vrba |
| 2004/0133232 A1 | 7/2004 | Rosenbluth et al. |
| 2004/0138696 A1 | 7/2004 | Drasler et al. |
| 2004/0153118 A1 | 8/2004 | Clubb et al. |
| 2004/0158278 A1 | 8/2004 | Becker et al. |
| 2004/0162576 A1 | 8/2004 | Barbut et al. |
| 2004/0164030 A1 | 8/2004 | Lowe et al. |
| 2004/0167567 A1 | 8/2004 | Cano et al. |
| 2004/0176794 A1 | 9/2004 | Khosravi |
| 2004/0176833 A1 | 9/2004 | Pavcnik et al. |
| 2004/0199203 A1 | 10/2004 | Oslund et al. |
| 2004/0204737 A1 | 10/2004 | Boismier et al. |
| 2004/0215322 A1 | 10/2004 | Kerr |
| 2004/0225321 A1 | 11/2004 | Krolik et al. |
| 2004/0236369 A1 | 11/2004 | Dubrul |
| 2005/0004663 A1 | 1/2005 | Llanos et al. |
| 2005/0027345 A1 | 2/2005 | Horan et al. |
| 2005/0038468 A1 | 2/2005 | Panetta et al. |
| 2005/0038503 A1 | 2/2005 | Greenhalgh |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009790 A1 | 1/2006 | Blake et al. |
| 2006/0009798 A1 | 1/2006 | Callister et al. |
| 2006/0020334 A1 | 1/2006 | Lashinski et al. |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0142845 A1 | 6/2006 | Molaei et al. |
| 2006/0184194 A1* | 8/2006 | Pal et al. .................... 606/200 |

| | | |
|---|---|---|
| 2006/0200221 A1 | 9/2006 | Malewicz |
| 2006/0229660 A1 | 10/2006 | Pal et al. |
| 2006/0264707 A1 | 11/2006 | Kinney |
| 2006/0287667 A1 | 12/2006 | Abela |
| 2006/0287668 A1 | 12/2006 | Fawzi et al. |
| 2007/0038241 A1 | 2/2007 | Pal |
| 2007/0100372 A1 | 5/2007 | Schaeffer |
| 2007/0112374 A1 | 5/2007 | Paul, Jr. et al. |
| 2007/0129752 A1 | 6/2007 | Webler et al. |
| 2007/0167974 A1 | 7/2007 | Cully et al. |
| 2007/0185521 A1 | 8/2007 | Bui et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | |
|---|---|---|
| EP | 1127556 A2 | 8/2001 |
| EP | 1310219 A2 | 5/2003 |
| EP | 1516601 | 3/2005 |
| EP | 1557137 A1 | 7/2005 |
| WO | WO 92/03097 | 3/1992 |
| WO | WO 96/10591 | 4/1996 |
| WO | WO 99/16382 | 4/1999 |
| WO | WO 99/23976 | 5/1999 |
| WO | WO 99/44510 | 9/1999 |
| WO | WO 01/82831 | 11/2001 |
| WO | WO 03/077799 A2 | 9/2003 |

OTHER PUBLICATIONS

Heeschen et al., Nature Medicine 7 (2001), No. 7, pp. 833-839.
Johnson et al., Circulation Research 94 (2004), No. 2, pp. 262-268.
International Search Report and Written Opinion for PCT/US2007/020300, Mar. 18, 2008.
Brochure, "Shuttle Select™ System for Carotid Artery Access," (2004), pp. 1-3.
Brochure, "Slip-Cath® Angiographic Selective Catheters," (2004), pp. 1-6.
Finol, E.A. et al., "Performance Assessment of Embolic Protection Filters for Carotid Artery Stenting," *Modelling in Medicine and Biology IV*, (2005), vol. 8, pp. 133.

* cited by examiner

HELICAL EMBOLIC PROTECTION DEVICE

BACKGROUND OF THE INVENTION

The present invention generally relates to medical devices. Particularly, the present invention relates to medical devices for embolic protection.

With the continuing advance of medical techniques, interventional procedures are more commonly being used to actively treat stenosis, occlusions, lesions, or other defects within a patient's blood vessels. Often the treated regions are in the coronary, carotid or even cerebral arteries. One procedure for treating an occluded or stenosed blood vessel is angioplasty. During angioplasty, an inflatable balloon is introduced into the occluded region. The balloon is inflated, pushing against the plaque or other material of the stenosed region and increasing the intralumenal diameter of the vessel. As the balloon presses against the material, portions of the material may inadvertently break free from the plaque deposit. These emboli may travel along the vessel and become trapped in a smaller blood vessel restricting blood flow to a vital organ, such as the brain.

Other methods for removing plaque or thrombus from arteries may include mechanical ablation, or non-contact ablation using light waves, sound waves, ultrasonics, or other radiation. Each of these methods are subject to the risk that some thrombogenic material may dislodge from the wall of the vessel and occlude a smaller blood vessel. The occlusion may cause damage to the patient, including an ischemic stroke in the cerebral arteries.

To prevent the risk of damage from emboli, many devices have been used to restrict the flow of emboli downstream from the stenosed area. One method includes inserting a balloon that may be expanded to occlude the flow of blood through the artery downstream of the stenosed area. An aspirating catheter may be located between the balloon and stenosed area and used to remove emboli that may be caused by the treatment. However, because the balloon completely blocks blood flow through the vessel, the vessel may be occluded only for short periods of time, limiting use of the procedure.

As an alternative to occluding flow through the blood vessel, various filtering devices have been proposed. Such devices typically have elements that form legs or a mesh that capture embolic material, but allow blood cells to flow between the elements. Capturing the emboli in the filter device prevents the material from being lodged downstream in a smaller blood vessel. The filter may then be removed along with the embolic material after the procedure has been performed and the risk from emboli has decreased.

Challenges also exist with filtering devices. Although adequate, many devices have various components connected together. In some situations, the number of components may add to the cross-section profile and the flexibility of the device. In view of the current challenges, it is apparent that there exists a need for an improved medical device for embolic protection.

BRIEF SUMMARY OF THE INVENTION

The present invention generally provides an embolic protection device for capturing emboli during treatment of a stenotic lesion in a body vessel. The present invention provides a device having a relatively small cross-sectional profile when being delivered or retrieved in a body vessel. Moreover, the present invention provides an emboli protection device that more effectively maintains trapped emboli therein during retrieval of the device.

In one embodiment, the present invention provides an embolic protection device for capturing emboli during treatment of a stenotic lesion in a body vessel comprising an elongated shaft. The elongated shaft has a proximal portion and a distal portion extending from the proximal portion. The device further comprises an expandable filter formed helically about the distal portion of the elongated shaft. The expandable filter is configured to helically close defining a collapsed state for delivery and retrieval of the device. The expandable filter is configured to helically open defining an expanded state for capturing emboli during treatment of the stenotic lesion in the body vessel. The expandable filter has at least one filter portion helically extending from the elongated shaft at a predetermined angle defining an opening when the filter is in the expanded state.

In another embodiment, the present invention provides an embolic protection assembly for capturing emboli during treatment of a stenotic lesion in a body vessel. The assembly comprises the emboli protection device mentioned above. The assembly further comprises a balloon catheter having a tubular body portion and an expandable balloon. The expandable balloon is attached to and in fluid communication with the tubular body portion for angioplasty at the stenotic lesion. The expandable balloon has distal and proximal portions.

In another example, the present invention provides a method for embolic protection during treatment of a stenotic lesion in a body vessel. The method comprises percutaneously introducing the balloon catheter in the body vessel. The method further comprises disposing the embolic protection device in the collapsed state coaxially within the balloon catheter. The method further comprises deploying the device in the expanded state by turning the elongated shaft about a first direction relative to the elongated shaft downstream from the stenotic lesion to helically open the expandable filter and capture emboli during treatment of the stenotic lesion.

Further objects, features, and advantages of the present invention will become apparent from consideration of the following description and the appended claims when taken in connection with the accompanying drawings.

BRIEF DESCRIPTION OF THE DRAWINGS

FIG. 1b is an enlarged environmental view of the device shown in FIG. 1a.

FIG. 2b is an enlarged view of the device in circle 2b of FIG. 2a.

FIG. 2c is an end view of the device in FIG. 2a.

FIG. 3b is an exploded view of the assembly in FIG. 3a.

FIG. 5d is an enlarged view of the device shown in circle 6b of FIG. 6a.

DETAILED DESCRIPTION OF THE INVENTION

The present invention generally provides an embolic protection device for capturing emboli during treatment of a stenotic lesion in a body vessel. Embodiments of the present invention provide a device having a reduced cross-sectional profile for delivery of the device during predilation of the stenotic lesion, and a more simple design of an integral device for capturing emboli from the body vessel. In one embodiment, the device includes an elongated shaft and an expandable filter formed helically about the distal portion of the elongated shaft. By rotation of the shaft, the expandable filter may be helically closed and helically opened, defining a collapsed state for delivery (and retrieval), and an expanded state for capturing emboli. The expandable filter has at least one filter portion, preferably a plurality thereof, that helically extends from the elongated shaft at a predetermined angle to define a proximally faced opening when the filter is in the expanded state.

Figure 1A:
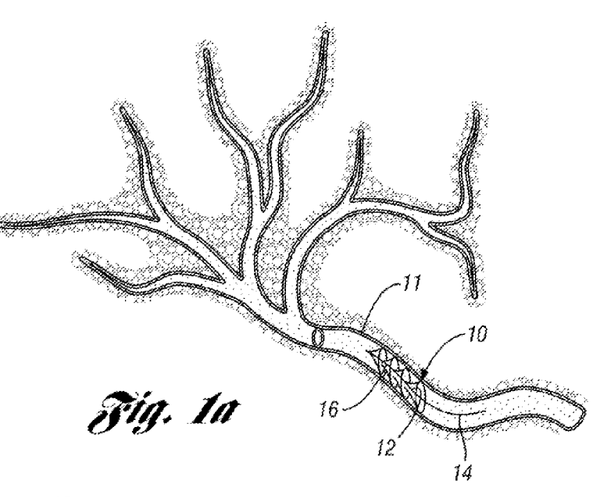
FIG. 1a is an environmental view of an emboli protection device for capturing emboli during treatment of a stenotic lesion in a body vessel in accordance with one embodiment of the present invention.
Figure 1B:
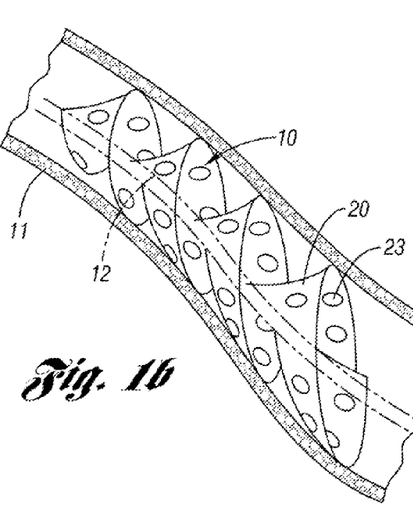
Figure 2A:
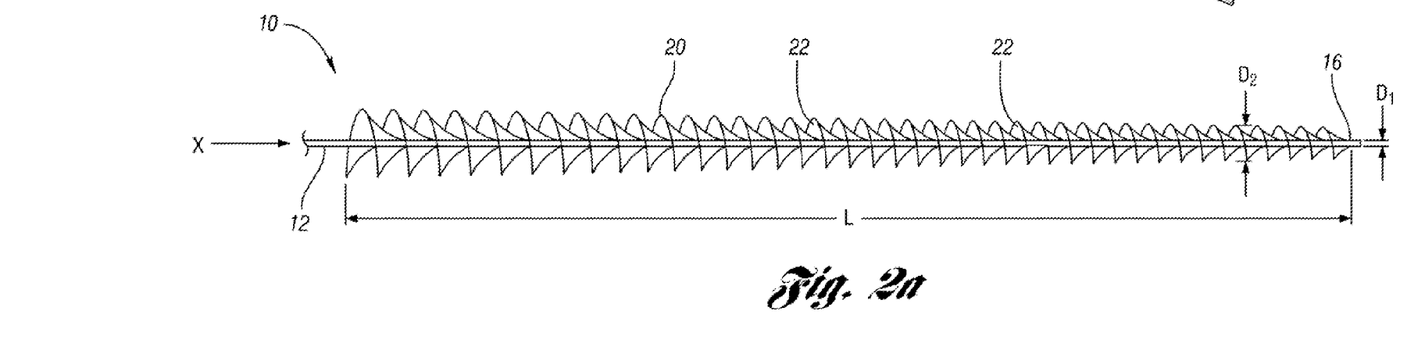
FIG. 2a is a side view of the embolic protection device depicted in FIGS. 1a and 1b.
Figure 2B:
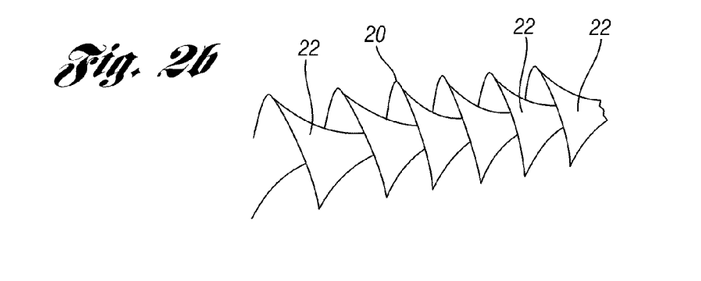
Figure 2C:
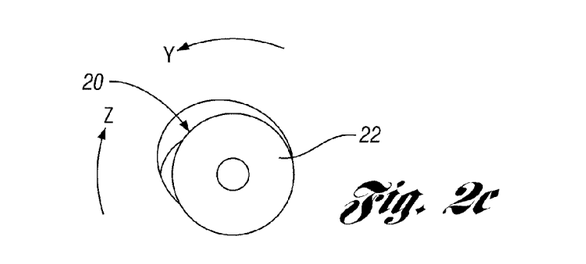
Figure 2D:
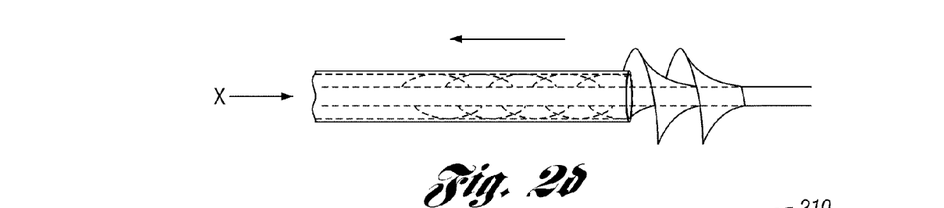
FIG. 2d is a side view of the device being partially deployed to an expanded state.

FIG. 1a illustrates an embolic protection device 10 for capturing emboli during treatment of a stenotic lesion in a body vessel 11 in accordance with one embodiment of the present invention. As shown, the device 10 comprises an elongated shaft 12 having a proximal portion 14 and a distal portion 16 extending distally from the proximal portion. In this embodiment, the elongated shaft 12 is tubular but may take on any other configuration such as having a core center without falling beyond the scope or spirit of the present invention. In this embodiment, the tubular shape of the elongated shaft 12 allows for a wire guide, for example, to be disposed therethrough for guidance during percutaneous introduction of the device in a body vessel. In this embodiment, the elongated shaft 12 has a first diameter $D_1$. As illustrated in FIGS. 2a-2b, the elongated shaft 12 includes a proximal portion 14 and a distal portion 16 extending from the proximal portion 14.

FIGS. 2a-2b further depict the device 10 further comprising an expandable filter 20 formed helically about the distal portion 16 of the elongated shaft 12. In this embodiment, the expandable filter 20 is formed integrally with the elongated shaft 12. This may be accomplished by any suitable means such as by machining a tubular body disposed about a mandrel to form the expandable filter about the elongated shaft. Other ways of forming the expandable filter about the elongated shaft may be used without falling beyond the scope or spirit of the present invention.

As shown in FIGS. 2a-2b, the expandable filter 20 has at least one filter portion 22, preferably a plurality of filter portions 22, that helically extends from the elongated shaft 12. In this embodiment, there is a plurality of filter portions 22 comprising the expandable filter 20. Each filter portion 22 helically extends from the elongated shaft at a predetermined angle, defining a proximally faced opening 24 when the filter 20 is in the expanded state. Each filter portion 22 defines a conical shape and overlaps with an adjacent filter portion 22. In this embodiment, the predetermined angle is between about 40 and 70 degrees, and preferably between about 55 and 65 degrees.

As shown, each of the plurality of filter portions 22 is in coaxial alignment with each other about the elongated shaft 12. Preferably, each filter portion 22 is helically formed integrally with the elongated shaft 12 and separately extends therefrom. This allows the elongated shaft 12 to maintain its flexibility with the first diameter $D_1$ for advancement through tortuous areas within a body vessel.

FIGS. 2a-2d illustrate that the expandable filter 20 and the elongated shaft 12 are formed along a longitudinal axis X. As mentioned, the expandable filter may be helically closed in the collapsed state when the elongated shaft 12 or the expandable filter 20 is rotated about the longitudinal axis in a first direction Y. The expandable filter 20 may be helically opened in the expanded state when the elongated shaft 12 or the expandable filter 20 is rotated about the longitudinal axis X in a second direction Z. The formation of the plurality of filter portions 22 provides the device 10 to more easily conform to the blood vessel tortuosity thereby allowing the device 10 to be more flexible. In this embodiment, each filter portion 22 comprises filter holes 23 formed therethrough to permit blood flow through the filter portion while restricting larger particles from passing therethrough. The holes 23 may have any size or shape without falling beyond the scope or spirit of the present invention.

As mentioned above, the device 10 may be made of shape memory material, or may be configured to have shape memory defining the predetermined shape thereof in the deployed state. For example, the device 10 may be comprised of any suitable material such as a pre-configured polymeric material, superelastic material, stainless steel wire, cobalt-chromium-nickel-molybdenum-iron alloy, or cobalt-chrome alloy. In one example, the device may be made of pre-configured polymeric material which takes on a predetermined shape, e.g. helical, when in the expanded state.

It is understood that the device may be formed of any other suitable material that may result in a self-opening or self-expanding device, such as shape memory materials or alloys. Shape memory alloys have the desirable property of becoming rigid, i.e., returning to a remembered state, when heated above a transition temperature. A shape memory alloy suitable for the present invention is Ni-Ti available under the more commonly known name Nitinol. When this material is heated above the transition temperature, the material undergoes a phase transformation from martensite to austenic, such that material returns to its remembered state. The transition temperature is dependent on the relative proportions of the alloy elements Ni and Ti and the optional inclusion of alloy additives.

In one example, the device is made from material including Nitinol with a transition temperature that is slightly below normal body temperature of humans, which is about 98.6° F. Thus, when the device 10 is deployed and exposed to normal body temperature, the alloy of the device will transform to austenite, that is, the remembered state, which for one embodiment of the present invention is the expanded state when deployed in the body vessel. To remove the device, the device is cooled to transform the material to martensite which is more ductile than austenite, making the device more malleable. As such, the device can be more easily collapsed and advanced or pulled into a lumen of a catheter for embolic protection.

Figure 3A:
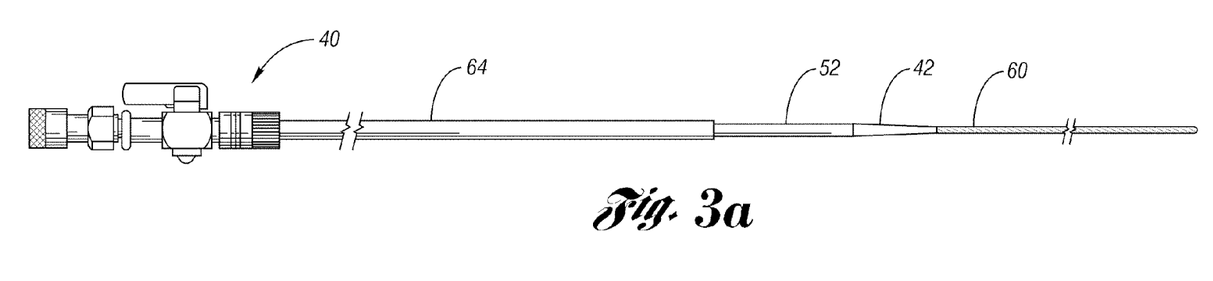
FIG. 3a is a side view of an embolic protection assembly for capturing emboli during treatment of a stenotic lesion in a body vessel in accordance with one embodiment of the present invention.
Figure 3B:
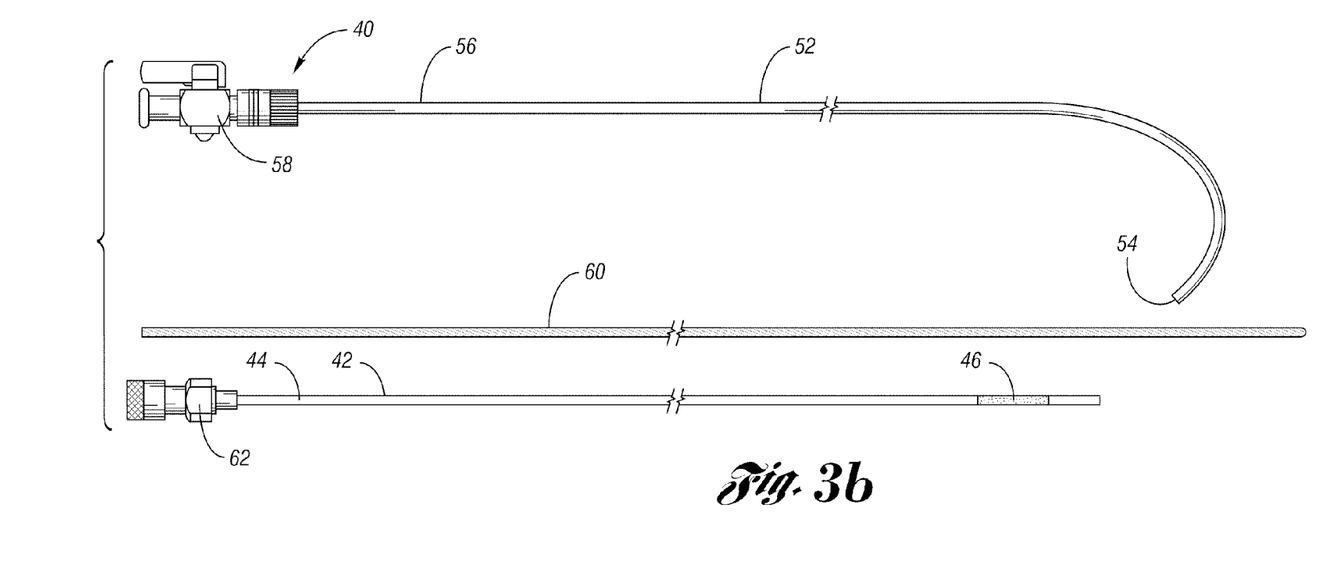

FIGS. 3a and 3b depict an embolic protection assembly 40 for capturing emboli during treatment of a stenotic lesion in a body vessel in accordance with another embodiment of the present invention. As shown, the assembly 40 comprises a balloon catheter 42 having a tubular body 44 and an expandable balloon 46 attached to and in fluid communication with the tubular body 44 for angioplasty at a stenotic lesion. In this embodiment, the assembly 40 comprises the embolic protection device mentioned above. The tubular body 44 is preferably made of soft flexible material such as silicon or any other suitable material. In this embodiment, the balloon catheter 42 includes an outer lumen and an inner lumen. The outer lumen is in fluid communication with the balloon 46 for inflating and deflating the balloon 46. The inner lumen is formed therethrough for percutaneous guidance through the body vessel.

As shown, the assembly 40 further includes an inner catheter 52 having a distal end 54 through which the balloon catheter 42 is disposed for deployment in the body vessel. The inner catheter 52 is preferably made of a soft, flexible material such as silicon or any other suitable material. Generally, the inner catheter 52 further has a proximal end 56 and a plastic adaptor or hub 58 to receive the embolic protection device and balloon catheter 42 to be advanced therethrough. The size of the inner catheter 52 is based on the size of the body vessel in which it percutaneously inserts, and the size of the balloon catheter 42.

As shown, the assembly 40 may also include a wire guide 60 configured to be percutaneously inserted within the vasculature to guide the inner catheter 52 to a location adjacent a stenotic lesion. The wire guide 60 provides the inner catheter 52 (and balloon catheter 42) a path during insertion within the body vessel. The size of the wire guide 60 is based on the inside diameter of the inner catheter 52.

In one embodiment, the balloon catheter 42 has a proximal fluid hub 62 in fluid communication with the balloon 46 via the outer lumen for fluid to be passed therethrough for inflation and deflation of the balloon 46 during treatment of the stenotic lesion.

As shown, the embolic protection device is coaxially disposed through the inner lumen of the balloon catheter 42 prior to treatment of the stenotic lesion in the body vessel. The distal protection device is guided through the inner lumen preferably from the hub 58 and distally beyond the balloon 46 of the balloon catheter 42, exiting from the distal end of the inner or balloon catheter 42 to a location within the vasculature downstream of the stenotic lesion.

In this embodiment, the apparatus further includes a polytetrafluoroethylene (PTFE) introducer sheath 64 for percutaneously introducing the wire guide 60 and the inner catheter 52 in a body vessel. Of course, any other suitable material may be used without falling beyond the scope or spirit of the present invention. The introducer sheath 64 may have any suitable size, e.g., between about three-french to eight-french. The introducer serves to allow the inner and balloon catheters 42 to be percutaneously inserted to a desired location in the body vessel. The introducer sheath 64 receives the inner catheter 52 and provides stability to the inner catheter at a desired location of the body vessel. For example, the introducer sheath 64 is held stationary within a common visceral artery, and adds stability to the inner catheter 52, as the inner catheter 52 is advanced through the introducer sheath 64 to a dilatation area in the vasculature.

When the distal end 54 of the inner catheter 52 is at a location downstream of the dilatation area in the body vessel, the balloon catheter 42 is inserted therethrough to the dilatation area. The device 10 is then loaded at the proximal end of the balloon catheter 42 and is advanced through the inner lumen thereof for deployment through its distal end. In this embodiment, the proximal stem is used to mechanically advance or push the device 10 through the catheter.

Figure 4:
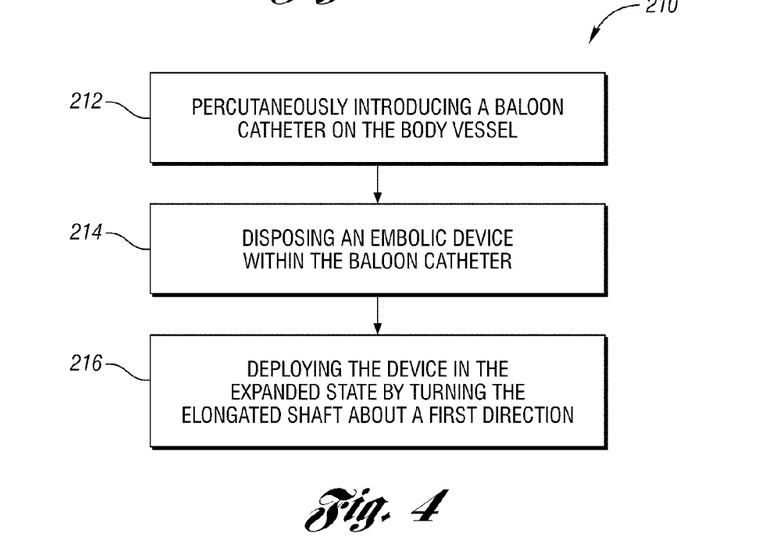
FIG. 4 is a flow chart of a method for embolic protection during treatment of a stenotic lesion in a body vessel in accordance with one example of the present invention.
Figure 4A:
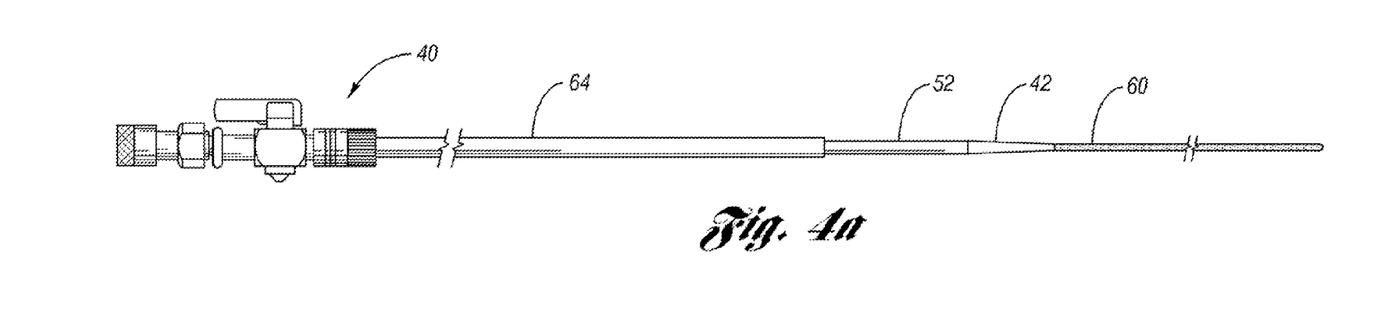
Figure 4B:
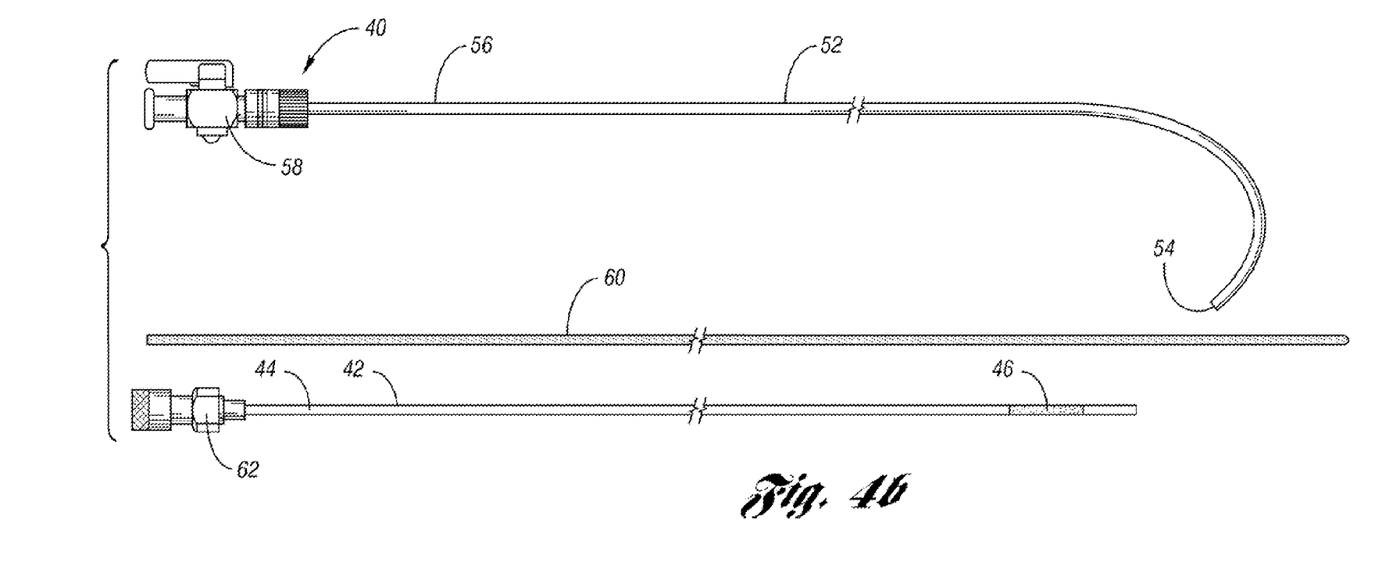
Figure 5A:
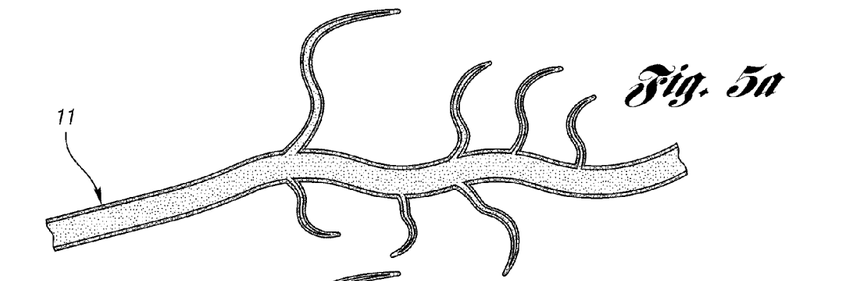
FIG. 5a is an environmental view of a body vessel in which the embolic protection assembly may be introduced.

FIG. 4 illustrates a flow chart depicting one method 210 for capturing emboli during treatment of a stenotic lesion in a body vessel (see FIG. 5a), implementing the assembly mentioned above. The method comprises percutaneously introducing a balloon catheter having an expandable balloon for angioplasty of the stenotic lesion in the body vessel in box 212. Introduction of the balloon catheter may be performed by any suitable means or mechanism. As mentioned above, an introducer sheath and a wire guide may be used to provide support and guidance to the balloon catheter. For example, the wire guide may be percutaneously inserted through the introducer sheath to the stenotic lesion in the body vessel. The balloon catheter may then be place over the wire guide for percutaneous guidance and introduction to the stenotic lesion.

Figure 5B:
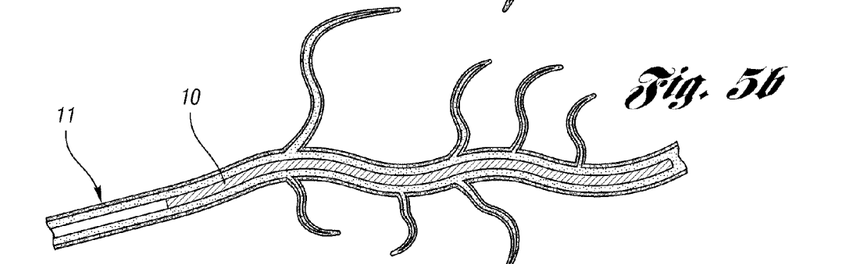
FIG. 5b is an environmental view of the embolic protection device in a collapsed state disposed in the body vessel of FIG. 4.

The method 210 further comprises disposing the embolic protection device coaxially within the balloon catheter in box 214. The device may be disposed coaxially within the balloon catheter before or after percutaneous insertion of the balloon catheter. For example, once the balloon catheter is placed at the stenotic lesion, the wire guide may be removed therefrom, and the device may then be disposed within the balloon catheter for guidance and introduction in the body vessel. In the collapsed state, the device may then be advanced distally past the balloon catheter in the body vessel (see FIG. 5b). In this example, the expandable balloon is positioned at the stenotic lesion and the device, in its collapsed state, is disposed through the distal end of the balloon catheter downstream from the expandable balloon.

Figure 5C:
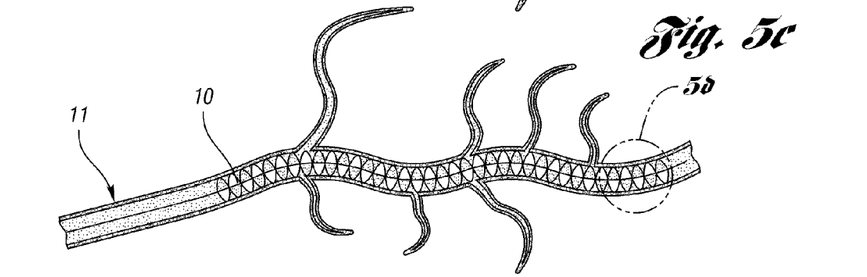
FIG. 5c is an environmental view of the embolic protection device in an expanded state disposed in the body vessel of FIG. 5.
Figure 5D:
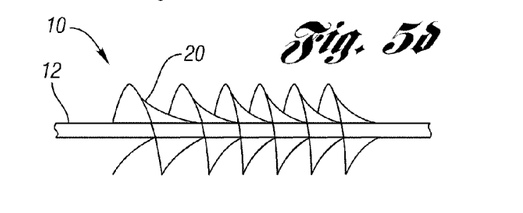

The method 210 further includes deploying the embolic protection device in the expanded state in box 216 (see also FIG. 5c). This may be accomplished by turning the elongated shaft about a first direction relative to the elongated shaft downstream from the stenotic lesion to helically open the expandable filter and capture emboli during treatment of the stenotic lesion in box 116. In the expanded state, the open end of each filter portion is expanded to a proximally facing concave shape to engage the body vessel for capturing emboli during angioplasty. In this embodiment, each filter portion extends from the elongated shaft at an angle between about 40 and 70 degree (see FIG. 5d).

The method may further include treating the stenotic lesion in the body vessel with the balloon catheter. As desired, additional balloon catheters may be used for primary and post-dilatation treatment of the stenotic lesion while the device is in its expanded state within the body vessel.

Figure 6:
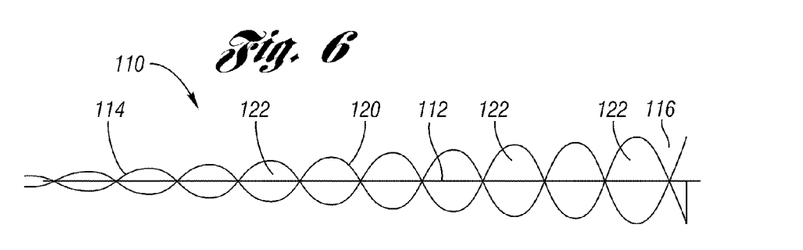
FIG. 6 is an embolic protection device for capturing emboli during treatment of a stenotic lesion in a body vessel in accordance with another embodiment of the present invention.

FIG. 6 illustrates an embolic protection device 110 having a varying second or outer diameter $D_2$ in accordance with another embodiment of the present invention. As shown, the device 110 has similar components as the device 10 mentioned above. For example the device 110 comprises an elongated shaft 112, a proximal portion 114, a distal portion 116, and an expandable filter 120 similar to the shaft 12, the proximal portion 14, the distal portion 16, and the expandable filter 20 of device 10. In this embodiment, each filter portion 122 includes a proximally faced opening having an outer diameter $D_2$ that increases distally. That is, the outer diameter $D_2$ increases distally longitudinally relative to the elongated shaft 112 to define the expandable filter 120 having a distally flared profile.

While the present invention has been described in terms of preferred embodiments, it will be understood, of course, that the invention is not limited thereto since modifications may be made to those skilled in the art, particularly in light of the foregoing teachings.

The invention claimed is:

1. An embolic protection device for capturing emboli during treatment of a stenotic lesion in a body vessel, the device comprising:
an elongated shaft having a proximal portion and a distal portion extending from the proximal portion; and
an expandable filter formed helically about the distal portion of the elongated shaft, the expandable filter formed integrally with the elongated shaft such that the elongated shaft and the expandable filter have a one-piece construction, the expandable filter being configured to helically close defining a collapsed state for delivery and retrieval of the device, the expandable filter being configured to helically open defining an expanded state for capturing emboli during treatment of the stenotic lesion in the body vessel, the expandable filter having a plurality of filter portions each helically and separately extending from the elongated shaft, the filter portions being directly adjacent to each other, each of the plurality of filter portions defining a proximally faced opening when the expandable filter is in the expanded state, the plurality of filter portions being of a one-piece construction with the elongated shaft and having filter holes formed therethrough, wherein each of the plurality of filter portions defines a conical shape and overlaps with an adjacent filter portion.

2. The device of claim 1 wherein the opening of each filter portion has an outer diameter, the outer diameter increasing distally longitudinally relative to the elongated shaft to define the expandable filter having a distally flared profile.

3. The device of claim 1 wherein the expandable filter extends along a longitudinal axis, the expandable filter being helically closed in the collapsed state when the elongated shaft is rotated about the longitudinal axis in a first direction, the expandable filter being helically opened in the expanded state when the elongated shaft is rotated about a second direction.

4. The device of claim 1 wherein the expandable filter comprises at least one of the following materials:
nitinol, elastomeric materials, polymeric materials.

5. The embolic protection device of claim 1 wherein the filter portions are not in direct contact with each other.

6. The embolic protection device of claim 5 wherein the plurality of filter portions comprises at least three filter portions.

7. The embolic protection device of claim 5 wherein the plurality of filter portions comprises at least four filter portions.

8. The embolic protection device of claim 1 wherein the plurality of filter portions comprises at least three filter portions.

9. The embolic protection device of claim 1 wherein the plurality of filter portions comprises at least four filter portions.

10. An embolic protection assembly for capturing emboli during treatment of a stenotic lesion in a body vessel, the assembly comprising
a balloon catheter having a tubular body portion and an expandable balloon attached to and in fluid communication with the tubular body portion for angioplasty at the stenotic lesion, the expandable balloon having distal and proximal portions; and
an embolic protection device coaxially disposed within the balloon catheter during treatment of the stenotic lesion in the body vessel, the device comprising:
an elongated shaft having a proximal portion and a distal portion extending from the proximal portion; and
an expandable filter formed helically about the distal portion of the elongated shaft, the expandable filter formed integrally with the elongated shaft such that the elongated shaft and the expandable filter have a one-piece construction, the expandable filter being configured to helically close defining a collapsed state for delivery and retrieval of the device, the expandable filter being configured to helically open defining an expanded state for capturing emboli during treatment of the stenotic lesion in the body vessel, the expandable filter having a plurality of filter portions each helically and separately extending from the elongated shaft at a predetermined angle relative to the elongated shaft, the filter portions being directly adjacent to each other, each of the plurality of filter portions defining a proximally faced opening when the expandable filter is in the expanded state, each of the plurality of filter portions having filter holes formed therethrough, each of the plurality of filter portions having a proximal end and a distal end, wherein the proximal end defines the opening in the expanded state, the proximal end being an open end free from contact of any other structure, wherein each of the plurality of filter portions defines a conical shape and overlaps with an adjacent filter portion.

11. The assembly of claim 10 wherein the balloon catheter includes an outer lumen and an inner lumen, the outer lumen being in fluid communication with the balloon for inflating and deflating the balloon, the inner lumen formed therethrough for percutaneous guidance through the body vessel.

12. The assembly of claim 10 further comprising:
an inner catheter having a distal end throughwhich the balloon catheter is disposed for deployment in the body vessel;
a wire guide configured to be disposed through the inner lumen of the balloon catheter for percutaneous guidance through the body vessel; and
an introducer sheath throughwhich the inner catheter is inserted for percutaneous insertion to the body vessel.

13. The assembly of claim 10 wherein the inner catheter further includes a proximal end, the proximal end having a hub in fluid communication with the balloon for fluid to be passed therethrough for inflation and deflation of the balloon during treatment of the stenotic lesion.

14. The device of claim 10 wherein the opening of each filter portion has an outer diameter, the outer diameter increasing distally longitudinally relative to the elongated shaft to define the expandable filter having a distally flared profile.

15. The device of claim 10 wherein the expandable filter extends along a longitudinal axis, the expandable filter being helically closed in the collapsed state when the elongated shaft is rotated about the longitudinal axis in a first direction, the expandable filter being helically opened in the expanded state when the elongated shaft is rotated about a second direction.

16. The device of claim 10 wherein the expandable filter comprises at least one of the following materials:
nitinol, elastomeric materials, polymeric materials.

17. The embolic protection assembly of claim 10 wherein the filter portions are not in direct contact with each other.

18. The embolic protection assembly of claim 10 wherein the plurality of filter portions comprises at least three filter portions.

19. A method for embolic protection during treatment of a stenotic lesion in a body vessel, the method comprising:
   percutaneously introducing a balloon catheter in the body vessel, the balloon catheter having a tubular body portion and an expandable balloon attached to and in fluid communication with the tubular body portion for angioplasty at the stenotic lesion;
   disposing an embolic protection device in a collapsed state coaxially within the balloon catheter, the device comprising:
   an elongated shaft having a proximal portion and a distal portion extending from the proximal portion; and
   an expandable filter formed helically about the distal portion of the elongated shaft, the expandable filter formed integrally with the elongated shaft such that the elongated shaft and the expandable filter have a one-piece construction, the expandable filter being configured to helically close defining the collapsed state for delivery and retrieval of the device, the expandable filter being configured to helically open defining an expanded state for capturing emboli during treatment of the stenotic lesion in the body vessel, the expandable filter having a plurality of filter portions each helically and separately extending from the elongated shaft at a predetermined angle relative to the elongated shaft, the filter portions being directly adjacent to each other, each of the plurality of filter portions defining a proximally faced opening when the expandable filter is in the expanded state, the plurality of filter portions being of a one-piece construction with the elongated shaft and having filter holes formed therethrough, wherein each of the plurality of filter portions defines a conical shape and overlaps with an adjacent filter portion; and
   deploying the device in the expanded state by turning the elongated shaft about a first direction relative to the elongated shaft downstream from the stenotic lesion to helically open the expandable filter and capture emboli during treatment of the stenotic lesion.

20. The method of claim 19 wherein the opening of each filter portion has an outer diameter, the outer diameter increasing distally longitudinally relative to the elongated shaft to define the expandable filter having a distally flared profile.

21. The method of claim 19 wherein the filter portions are not in direct contact with each other.

* * * * *